United States Patent [19]
Kokko et al.

[11] Patent Number: 4,698,429
[45] Date of Patent: Oct. 6, 1987

[54] ALKYLATED 8-HYDROXYQUINOLINE DERIVATIVES VIA A DIELS-ALDER CYCLOADDITION TO 5,7-DIALLYL OR 7-ALLYL SUBSTITUENTS THEREON

[75] Inventors: Kent S. Kokko, Shoreview; Phillip L. Mattison, New Brighton, both of Minn.

[73] Assignee: Henkel Corporation, Ambler, Pa.

[21] Appl. No.: 804,403

[22] Filed: Dec. 3, 1985

[51] Int. Cl.[4] ........................................... C07D 215/26
[52] U.S. Cl. ..................................... 546/179; 423/24; 423/DIG. 14
[58] Field of Search ......................................... 546/179

[56] References Cited

U.S. PATENT DOCUMENTS

| 3,637,771 | 1/1972 | Badde et al. | 546/179 |
| 4,045,441 | 8/1977 | Richards et al. | 546/179 |
| 4,065,455 | 12/1977 | Mattison | 546/179 |
| 4,066,652 | 1/1978 | Hartlage | 546/179 |

Primary Examiner—Glennon H. Hollrah
Assistant Examiner—D. B. Springer
Attorney, Agent, or Firm—Ernest G. Szoke; Patrick J. Span

[57] ABSTRACT

Substituted 8-hydroxyquinoline metal extractants having a cyclic hydrocarbon substituent at either the 5 and 7 or only the 7 position are described.

8 Claims, No Drawings

ALKYLATED 8-HYDROXYQUINOLINE DERIVATIVES VIA A DIELS-ALDER CYCLOADDITION TO 5,7-DIALLYL OR 7-ALLYL SUBSTITUENTS THEREON

BACKGROUND OF THE INVENTION

1. Field of the Invention

This invention relates to the preparation of 8-hydroxyquinolines and their use as metal extractants.

2. Statement of the Related Art

Substituted and non-substituted 8-hydroxyquinoline compounds are well-known for their ability to coordinate with ions of a variety of transition metals to form relatively stable complexes commonly referred to as metal chelates. This complexing technique has been used extensively in chemical analytical procedures. Chelates have also been utilized in hydrometallurgical extraction processes applicable for the recovery of metal values from aqueous solutions thereof. These extraction processes comprise basically a two step operation. In the first step an impure aqueous phase containing the desired metal values in ionic form is contacted with a water-immiscible organic solution of the extractant whereby the metal ions are extracted into the organic phase to form a chelate with the organic extractant. The second step, referred to as stripping, transfers the extracted metal values into an aqueous phase regenerating the metal ions, and forming a relatively concentrated solution of the desired metal. The metal can then can then be recovered from this solution by any convenient recovery method, such as electrolysis.

Substituted 8-hydroxyquinolines compounds having bulky hydrocarbon substituents are used to enhance the hydrocarbon solubility characteristics of the 8-hydroxyquinoline. Substituents selected on the basis of their carbon atom content will reduce the extractant's solubility in strongly acidic aqueous mediums and increase hydrocarbon solubility. The molecular configuration of the substituent, moreover, can be used to increase the loading capabilities of the base compound.

One example of such substituted 8-hydroxyquinoline extractant is described in U.S. Pat. No. 3,637,711. This patent describes substituted 8-hydroxyquinolines characterized by having a beta-alkenyl group in the number 7 position. A similar substituted 8-hydroxyquinoline also used in metal extraction is described in U.S. Pat. No. 4,066,652, describing a class of alpha-alkenyl substituted 8-hydroxyquinolines.

One disadvantage of these extractants is encountered with hydroxyquinolines having alpha- or beta- unsaturated hydrocarbon substituents in the 7 position. This unsaturation, moreover, is difficult or impossible to remove, even by hydrogenation. These alkenyl substituted 8-hydroxyquinolines have the disadvantage of instability, especially when contacted with strong alkali and air at elevated temperatures. Such conditions cause the double bond in the side chain to slowly react with the phenolic oxygen in the 8 position to form a cyclic ether having little or no activity as a solvent extraction reagent. An extractant without the alpha- or beta- unsaturation on the 7-position substituent, therefore, would have significant advantages in metal recovery, especially if this extractant also has an enhanced hydrocarbon solubility.

The instant invention describes substituted 8-hydroxyquinoline derivatives having a hydrocarbon substituent in the 7-position which does not have alpha or beta unsaturation. It is also an object of the instant invention to provide alkylated 8-hydroxyquinoline derivatives which can have increased organic solubility by the addition of further saturated or unsaturated hydrocarbon moieties to the compound. The instant invention also provides substituted 8-hydroxyquinoline metal extractants which can have a variety of substituted or unsubstituted cyclic hydrocarbon sturctures. This provides a useful tool for varying activity, solvents, and other extractant characteristics. Other objects will become apparent as this description proceeds.

BRIEF DESCRIPTION

Substituted 8-hydroxyquinoline compounds which are useful as metal extractants, can be made having the formula:

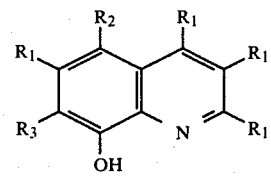

FIG. 1 wherein each $R_1$ can be the same or different and are selected from the group consisting of: a hydrogen, a halogen and a saturated aliphatic hydrocarbon; wherein $R_2$ is selected from the group consisting of: hydrogen, $R_3$, and a halogen, a saturated aliphatic hydrocarbon, and where $R_3$ is a substituent formed by a cycloaddition reaction between a conjugated diene and a dienophile. $R_3$ is therefore a hydrocarbon adduct containing the characteristic cyclic ring structure left by the cycloaddition reaction. $R_3$ has at least one of these ring structures formed in a cycloaddition reaction. At least one unsaturated bond is also characteristic of the ring structure formed in the cycloaddition reaction. This unsaturation, however, can easily be removed by further reaction since the double bond is in a more accessible position after the cycloaddition. Such further reactions include hydrogenation or halogenation. Halogenation of the unsaturated $R_3$ adduct can be advantageously performed to vary the performance of the metal extracting compound.

The reaction producing the above metal extracting compounds, and forming $R_3$ is a cycloaddition reaction between (a) a hydrocarbon compound containing a conjugated diene, and (b) a dienophile moiety which is a substituent of the 8-hydroxyquinoline. This dienophile substituent is an unsaturated hydrocarbon found in the 7, or 5 and 7 positions of the 8-hydroxyquinoline. This cycloaddition reaction between a dienophile and a conjugated diene is well-known, and is frequently described as the Diels-Alder reaction.

The above described metal extractants can be used to extract metals, such as copper, gallium, germanium and zinc from solutions by contacting the metal-containing aqueous solutions with an organic solution containing a water-immiscible organic solvent and the instant cyclo-substituted 8-hydroxyquinolines. Extraction conditions can be varied to favor one metal over others. When the organic solution containing the metal extractants of the instant invention contacts the aqueous solution containing the metal values, said metal values will be extracted into the organic solution and form chelates with the instant extractants. The two phases are then separated.

The metal values can then be stripped from the separated organic phase and then recovered.

DETAILED DESCRIPTION

The above described extractants can be made by conducting a cycloaddition reaction between (a) a conjugated diene and (b) a compound having the formula:

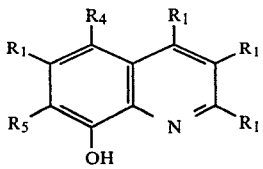

FIG. 2 wherein each $R_1$, as previously indicated, can be the same or different and are selected from the group consisting of: a hydrogen, a halogen and a saturated aliphatic hydrocarbon; $R_4$ is selected from the group consisting of a $R_1$ and $R_5$, and wherein $R_5$ is the dienophile moiety. When $R_1$ and $R_2$ (of FIG. 1) are saturated hydrocarbons; the saturated hydrocarbon substituent suitably has from 1 to 16 hydrocarbons; preferably it has from 1 to 12 hydrocarbons The dienophile moiety is characterized by the $2\pi$ (pi) electrons which react with the conjugated diene. The unsaturation of this dienophile moiety can be in the alpha- or beta- position from the ring of the 8-hydroxyquinoline or can be the pi bond remaining from a previous Diels Alder cycloaddition reaction. Suitably, this dienophile moiety ($R_5$) can be an alkenyl group having from 2 to 20 carbon atoms; preferably it has from 2 to 14 carbon atoms, and most preferably has from 2 to 8 carbon atoms. Representative examples of these dienophile substituents are ethenyl, propenyl, butenyl, pentenyl and hexenyl.

Suitable alpha- or beta- alkenyl substituted 8-hydroxyquinolines can be prepared by conventional techniques; 7-allyl-8-quinolinol, for example, can be prepared by the reaction of 8-quinolinol with allyl chloride in the presence of a suitable catalyst such as sodium iodide at temperatures of 40°-80° C..

A conjugated diene can be defined as an unsaturated hydrocarbon system having at least $4\pi$ (Pi) electrons wherein double bonds are separated only by a single bond. An example of a conjugated diene is 1,3-butadiene. Any conjugated diene can be used in this reaction to produce the extractants of the instant invention. Suitably conjugated dienes will have from 4 to 20 carbon atoms, and preferably the conjugated diene has from 4 to 10 carbon atoms. Acceptably, the following dienes can be used: 1,3-butadiene, 1,3-pentadiene, cyclohexadiene, cyclopentadiene and anthracene. The cycloaddition reaction can be conveniently conducted using conventional techniques. Accordingly, temperatures are suitably in the range of from about 15° C. to 250° C., with pressures of from about 1 to about 5 atmospheres. Preferably, an organic solvent is used.

In preparing the instant extractants the conjugated diene and the 8-hydroxyquinoline having the dienophile substituent can suitably be reacted at concentrations used conventionally for Diels-Alder cycloaddition reactions. Preferably the conjugated diene is used in a larger amount than the dienophile substituted 8-hydroxyquinolines. Thus, a preferred concentration ratio of the conjugated diene to the dienophile moiety is in the range of from about 1:1 to 5:1.

After the first cycloaddition reaction, one or more further cycloaddition reactions can be completed using reactive conditions and conjugated diene reagents as previously indicated. Further cycloadditions will increase hydrocarbon affinity and will result in more cyclic hydrocarbon structures in the $R_3$ substituent of the above described metal extracting compounds.

After one cycloaddition reaction has been completed on a substituted 8-hydroxyquinoline having an alkenyl substituent in the 7 or 5 and 7 position, the pi bond, which is usually in the alpha- or beta-position from the ring of the alkenyl-substituted 8-hydroxyquinoline will have been moved away from the ring as a result of the cycloaddition reaction. If desired, therefore, hydrogenation can now be done in order to substantially remove the unsaturation. Conventional hydrogenation techniques can be used. It should be noted, however, that after even one cycloaddition reaction, the unsaturation is no longer in the alpha-or beta- position to the ring making the substituent of $R_3$ less subject to the oxygenating conditions caused by the proximity of the hydroxyl group. Thus the compounds of the instant invention are useful, more stable metal extractants even without the additional hydrogenation reaction.

After cycloaddition, the resulting product can also be subjected to further reactions serving to optimize particular performance characteristics of these metal extracting compounds. In fact, the unsaturated bond of the cycloaddition adduct can be subjected any additional reaction typical for alkenes. Thus, the new substituent ($R_3$) can be chemically varied since the double bond of the cycloaddition adduct is more removed from the ring. Halogenation, for example, can be performed on the instant metal extracting cycloaddition adduct. Such reactions can be used to influence the characteristics of the compounds and their metal extracting capabilities. Any technique useful for the addition of a halide onto an unsaturated hydrocarbon can be used. Suitable conditions can be found described in *Advanced Organic Chemistry by J. March*. Hydrohalogenation will result in the addition of halides to the cycloaddition adduct at the point of unsaturation. Halides which can be added include chloride, bromide, fluoride and iodide. Of these, the most preferred is chloride.

If desired, the cycloaddition adduct of $R_3$ can also be alkylated using techniques suitable of alkyl groups to unsaturated hydrocarbons.

The examples which follow are offered to illustrate the instant invention and not to limit it. All parts and percentages are by weight unless otherwise specified.

EXAMPLES

Example 1

A quantity of 185 grams (g) of 7-allyl-8-hydroxyquinoline was dissolved in xylene and charged into a stirring autoclave, and 1.5 moles of dicyclopentadiene in a solution of xylene was added by pump over a 24 hour period. The temperature was maintained at 190° C. as the reaction continued. After the reaction, the product was cooled to room temperature, and gas chromotography was used to confirm the following structure:

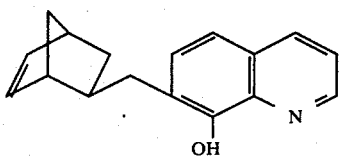

Example 2

A quantity of 225 g of 5,7-bis allyl hydroxyquinoline was dissolved in xylene and charged into a stirring autoclave, and 1.5 moles of dicyclopentadiene in a solution of xylene was added by pump over a 24 hour period. The temperature was maintained at 190° C. as the reaction continued. After the reaction, the product was cooled to room temperature, and gas chromotography was used to confirm the following structure:

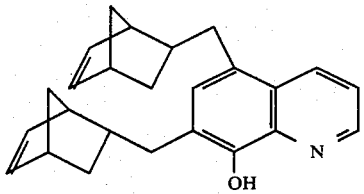

Example 3

One gram of the 5,7 cyclo adduct produced in Example 2 and 2.5 g. of isodecanol was diluted to 20 milliliters (mL) with kerosene. An acidic copper feed solution was prepared containing 6 gram/liter Cu and 3 gram/liter Fe (pH=2); and the immiscible organic solution containing the extractant was contacted with four successive equal volumes of this copper-containing feed solution. At this point, atomic absorption indicated that the immiscible organic extractant solution contained .41% Cu and 0.0093% Fe.

The copper-loaded extractant solution was then subjected to stripping conditions to remove the copper by contacting this copper-loaded solution with an aqueous solution containing 30 g/l Cu and 170 g/l $H_2SO_4$. After stripping atomic absorption analysis of the stripped organic extractant solution now indicated that the amount of the copper has dropped to 0.009%.

What is claimed is:

1. A compound produced from the Diels-Alder reaction at temperatures of about 15°-250° C. and a pressure of about 1-5 atmospheres of (a) a conjugated hydrocarbon having from 4-20 carbon atoms and (b) an 8-hydroxyquinoline of the formula:

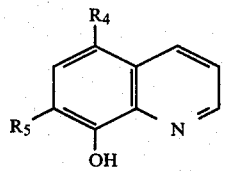

wherein $R_4$ is hydrogen and $R_5$ is allyl to provide a compound of the formula

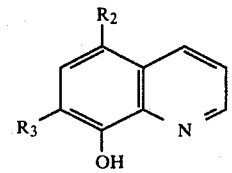

where $R_2$ is selected from the group consisting of hydrogen and $R_3$ and wherein $R_3$ is the residual hydrocarbon radical remaining from the reaction of said conjugated diene and said $R_5$.

2. A compound produced as defined in claim 1 wherein $R_2$ is hydrogen, $R_5$ is allyl and $R_3$ is residual hydrocarbon moiety remaining from the reaction of dicyclopentadiene and said allyl group.

3. A compound produced as defined in claim 1 wherein $R_3$ is subsequently hydrogenated to remove unsaturation therein.

4. A compound produced from the Diels-Alder reaction at temperatures of about 15°-250° C. and a pressure of about 1-5 atmospheres of (a) a conjugated hydrocarbon diene having from 4-20 carbon atoms and (b) an 8-hydroxyquinoline of the formula:

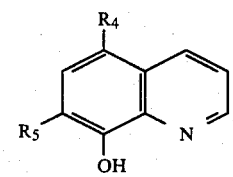

wherein both $R_4$ and $R_5$ are allyl groups to provide a compound of the formula

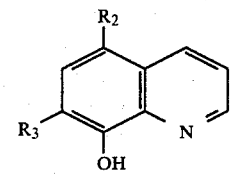

wherein each of $R_2$ and $R_3$ residual hydrocarbon radical remaining from the reaction of said conjugated diene and said allyl groups $R_4$ and $R_5$.

5. A compound as defined in claim 4 and $R_3$ is the residual hydrocarbon moiety remaining from the reaction of dicyclopentadiene and said allyl groups.

6. A compound produced as defined in claim 4 wherein $R_2$ and $R_3$ are subsequently hydrogenated to remove unsaturation therein.

7. A compound produced from the Diels-Alder reaction at temperatures of about 15°-250° C. and a pressure of about 1-5 atmospheres of (a) a conjugated hydrocarbon diene having from 4-20 carbon atoms and (b) an 8-hydroxyquinoline of the formula:

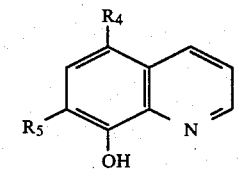

wherein R₅ is an allyl group and R₄ is selected from the group consisting of hydrogen and R₅, to provide a compound of the formula:

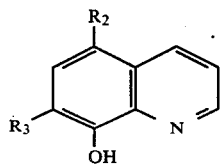

where R₂ is selected from the group consisting of hydrogen and R₃ and wherein R₃ is the residual hydrocarbon radical remaining from the reaction of said conjugated diene and said R₅.

8. A compound produced from the Diels-Alder reaction at temperatures of about 15°–250° C. and a pressure of about 1–5 atmospheres of (a) a conjugated diene selected from the group consisting of 1,3-butadiene, 1,3-pentadiene, cyclopentadiene, dicyclopentadiene, 1,3-cyclohexadiene and anthracene and (b) an 8-hydroxyquinoline of the formula:

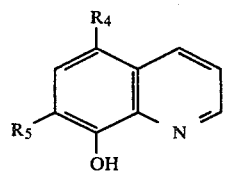

to provide a compound of the formula

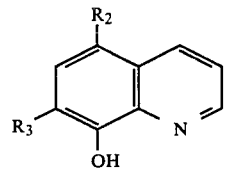

wherein R₅ is an allyl group, R₄ is selected from hydrogen and R₅ and R₂ is selected from the group consisting of hydrogen and R₃ and wherein R₃ is the residual hydrocarbon radical remaining from the reaction of said conjugated diene and R₅.

* * * * *